(12) United States Patent
Balder et al.

(10) Patent No.: US 10,111,464 B1
(45) Date of Patent: Oct. 30, 2018

(54) BROILER-TYPE HEATING DEVICE FOR ELECTRONIC VAPING

(71) Applicant: Healthier Choices Management Corp., Hollywood, FL (US)

(72) Inventors: Edwin Balder, Mesa, AZ (US); Gilbert Cyphert, Phoenix, AZ (US); Daniel Julia, Phoenix, AZ (US)

(73) Assignee: HEALTHIER CHOICES MANAGEMENT CORP, Hollywood, FL (US)

( * ) Notice: Subject to any disclaimer, the term of this patent is extended or adjusted under 35 U.S.C. 154(b) by 0 days.

(21) Appl. No.: 15/895,755

(22) Filed: Feb. 13, 2018

Related U.S. Application Data (63) Continuation-in-part of application No. 15/832,582, filed on Dec. 5, 2017.

(51) Int. Cl.
| | | |
|---|---|---|
| A24F 47/00 | (2006.01) |
| A61M 15/06 | (2006.01) |
| A61M 11/04 | (2006.01) |
| A24F 1/32 | (2006.01) |
| A61M 15/00 | (2006.01) |
| A24F 3/02 | (2006.01) |

(52) U.S. Cl.
CPC .............. *A24F 47/004* (2013.01); *A24F 1/32* (2013.01); *A61M 11/041* (2013.01); *A61M 15/0021* (2014.02); *A24F 3/02* (2013.01)

(58) Field of Classification Search
CPC ................................ A24F 47/00; A61M 15/06
See application file for complete search history.

(56) References Cited

U.S. PATENT DOCUMENTS

| | | | |
|---|---|---|---|
| 7,832,410 B2 | 11/2010 | Hon | |
| 2015/0020832 A1* | 1/2015 | Greim | A24F 47/008 131/329 |

FOREIGN PATENT DOCUMENTS

| | | |
|---|---|---|
| CN | 102423145 | 4/2012 |

\* cited by examiner

*Primary Examiner* — Cynthia Szewczyk
(74) *Attorney, Agent, or Firm* — Lewis Brisbois Bisgaard & Smith, LLP; Geoffrey Lottenberg (57) ABSTRACT

A broiler-type heating device for electronic smoking devices such as electronic cigarettes and vaporizers includes a heating element located above the storage area where the inhalant material is located. The heating element is in electrical communication with a lower connector located below the storage area. A partition defines the bottom of the internal storage area and separates the storage area from the lower connector. The heating device may be two separate pieces, a chamber and a cradle, that are removably connected. The heating element is located in the chamber above the storage area, which is located in the cradle.

5 Claims, 7 Drawing Sheets

BROILER-TYPE HEATING DEVICE FOR ELECTRONIC VAPING

This application is a continuation-in-part of U.S. patent application Ser. No. 15/832,582, filed Dec. 5, 2017.

FIELD OF THE INVENTION

The present invention relates to electronic cigarettes and vaporizers.

BACKGROUND OF THE INVENTION

In an attempt to solve the problems of traditional smoking, electronic cigarettes and vaporizers have come to the forefront. These devices employ the use of a liquid, concentrate, or dry material inhalants that often comprise glycol ad-mixtures, wax-like substances, herbs, flowers, and other medicinal substances. In the conventional art, the inhalant is placed on or otherwise drawn to and over a metal heating element, such as a metal coil, which coil receives electrical energy from an on-board battery. The electrical energy is converted to heat, thereby heating and vaporizing the inhalant material brought in contact with the heating element. The resultant vapor, smoke, or other aerosol is then inhaled by way of a mouthpiece in fluid communication with an air channel disposed through the device.

In most electronic cigarettes and vaporizers, the inhalant material is brought into direct contact with the heating element, which heats and often burns or combusts the inhalant material through conduction. The downside of these electronic cigarette and vaporizer systems is that repeated heating and cooling of the metal heating element will cause transfer of heavy metals into the resultant vapor or smoke, resulting in inhalation of harmful and unwanted heavy metal material. Recent studies have in fact shown that heavy metal exposure caused by traditional electronic cigarettes and vaporizers is as harmful as or possibly more harmful than exposure to the carcinogens found in traditional cigarettes.

In addition to the toxicity issues associated with direct contain between the target inhalant material and the metal heating coil, traditional electronic cigarette and vaporizer systems suffer from degradation of and eventual loss of performance due to waste buildup on the metal coil and the surrounding area. As the buildup continues to develop, the device tends to generate less available smoke or vapor and the flavor and "hit" consistency will be impacted. Sooner than later the metal coil will need to be cleaned using toxic chemicals or, in most cases, will need to be replaced regularly.

In other systems, such as those described in Applicant's U.S. patent application Ser. Nos. 13/987,851 and 15/832,582, each of which is herein incorporated by reference (among others as specifically set forth and identified herein), indirect heating of the inhalant material is accomplished by providing an electronic cigarette and/or vaporizer system wherein the inhalant material disposed above and at least somewhat spaced apart from the heating element, such that the heating element in effect "bakes" the inhalant material. By that, baking denotes that the heat source is disposed beneath the inhalant material such that convection due to the rising heat is sufficient to heat the inhalant material for inhalation. While "baking"-type systems are useful and efficient, in certain circumstances the baking configuration can cause an overflow of inhalant material or inefficient heating to the point where the inhalant material undesirable falls down onto or otherwise makes direct contact with the heating element or portions of the inhalant material remain unheated or partially heated, to the detriment of the overall smoking experience.

Accordingly, the present invention is directed at an alternative to the "burn"-type and "bake"-type electronic cigarettes and vaporizer systems. Namely, the present invention contemplates various embodiments of a broiler-type heating device for electronic cigarettes and vaporizer systems.

It will be recognized that some or all of the Figures are schematic representations for purposes of illustration and do not necessarily depict the actual relative sizes or locations of the elements shown. The Figures are provided for the purpose of illustrating one or more embodiments of the invention with the explicit understanding that they will not be used to limit the scope or the meaning of the claims.

DETAILED DESCRIPTION

In the following description, for the purposes of explanation, numerous specific details are set forth in order to provide a thorough understanding of the present invention. It will be apparent, however, to one skilled in the art that the present invention may be practiced without some of these specific details. Throughout this description, the embodiments and examples shown should be considered as exemplars, rather than as limitations. That is, the following description provides examples, and the accompanying drawings show various examples for the purposes of illustration. However, these examples should not be construed in a limiting sense as they are merely intended to provide examples of the present invention rather than to provide an exhaustive list of all possible implementations.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "some embodiments" or "one embodiment" or "an embodiment" means that a particular feature, structure or characteristic described in connection with the embodiment is included in at least one embodiment of the present invention. Thus, appearances of the phrases "in some embodiments" or "in an embodiment" in various places throughout this specification are not necessarily all referring to the same embodiment. Furthermore, the particular features, structures or characteristics may be combined in any suitable manner in one or more embodiments.

For purposes of this disclosure, the terms "electronic cigarette" and "vaporizer" are interchangeable and generally refer to an electronic device configured to heat a target inhalant material to be inhaled by the user by mouth. "Inhalant material" for purposes of this disclosure refers to any desired material to be heated and inhaled by way of the electronic cigarette or vaporizer. Such materials include, without limitation, liquids such as glycol-based solutions, semi-solid or solid concentrates such as oils and waxes, shatter, and dry material such as tobacco, herbs, flowers, and aromatics. The term "vaping" refers generally to the act of using electronic cigarettes and vaporizers for the purposes of generating vapor, smoke, aerosol or other material to be inhaled for pleasure or for the delivery of medicaments or substances to the body; notably, the term is not limited to the act of generating or inhaling only vapor—it refers more broadly to the act of inhaling material by way of electronic devices, as opposed to traditional smoking implements such as cigarettes, pipes, cigars, and the like.

Figure 1A:
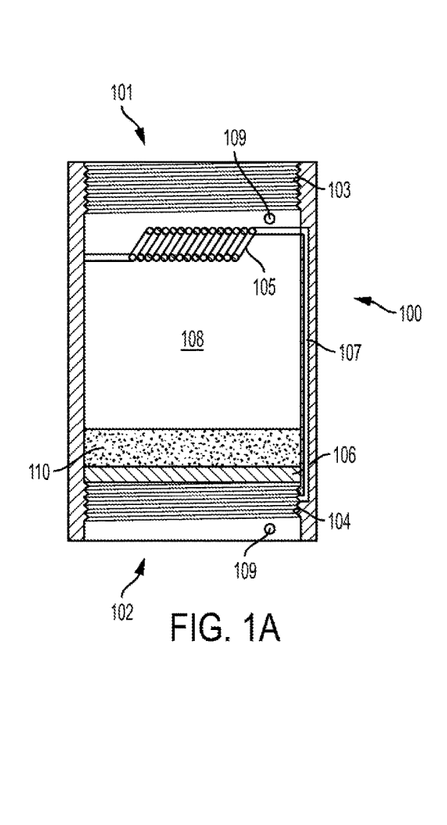
FIG. 1A is a cutaway view of one embodiment of the heating device.
Figure 1B:
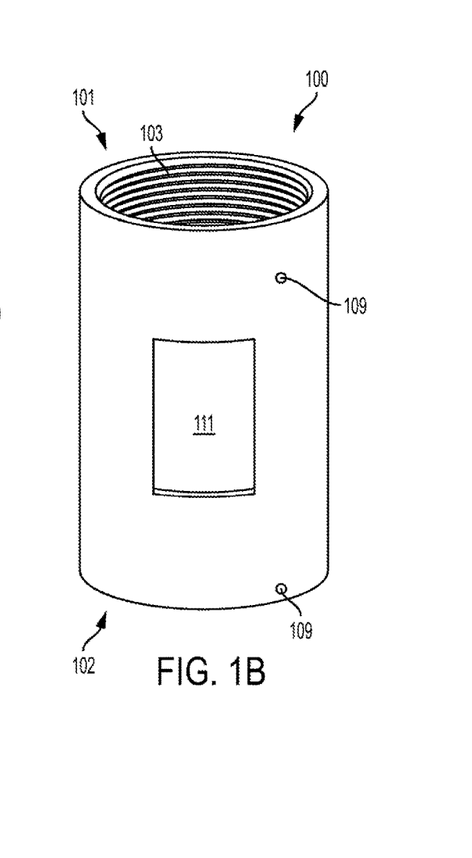
FIG. 1B is a perspective view of the heating device shown in FIG. 1A.

With reference to FIGS. 1A-1B shown is an embodiment of a heating device 100 configured as a "one-piece" heating device. In some embodiments, the heating 100 has an upper connector end 101 and a lower connector end 102. The upper connector end 101 includes an upper connector 103 and the lower connector end includes a lower connector 104. The connectors 103 and 104 can each be either male or female and are configured to engage other components of an electronic smoking device system, such as a battery or other power supply and/or a control unit or mouthpiece as further described herein.

Disposed adjacent to the upper end 101 is a heating element 105. In some embodiments, the upper connector 103 is disposed above the heating element 105. The heating element 105 is in electrical communication with at least the lower connector end 102 such that the heating element 105 can be put into electrical communication with a battery or other power supply. In some embodiments, for example, an electrical connector 107 electrically couples the respective anode and cathode of the heating element to the lower connector 104, which lower connector 104 is configured as a respective anode and cathode connector to engage corresponding fittings on a battery or other power supply. The electrical connector 107 is not limited in configuration, however in some examples it may comprise wiring or a ribbon-type electrical conduit disposed in the sidewall (in the vicinity of where call out 107 points) of the device 100.

Disposed below and beneath the heating element 105 is an internal storage area 108 wherein inhalant material 110 (shown for exemplary purposes) may be placed. In some embodiments, the lower connector 104 is disposed below the internal storage area 108. In some embodiments, a partition 106 is disposed substantially toward the bottom of the internal storage area 108, which partition 106 functions as the floor, bottom, or shelf of the storage area 108 and separates same from the lower connector 104. Additionally shown disposed through the device 100 are one or more air passages 109 which promote airflow through the heating device 100 while in use. The air passages 109 may be configured as apertures disposed through the housing of the heating device 100 although other configurations are possible, such as a slots or bores located about the upper and/or lower connector ends 101 and 102. Accordingly, in some embodiments the heating device 100 includes at least one air passage 109.

With reference to FIG. 1B, shown is an exterior perspective view of the heating device 100. In some embodiments, the heating device 100 includes an access door 111 to permit access to the internal storage area 108 in order to deposit or insert inhalant material. In some embodiments, the door 11 is configured to manually slide and retract into the adjacent area of the housing of the heating device 100. In other embodiments, the door 111 may be hingeably connected to adjacent structure of the housing of the heating device 100.

Figure 2A:
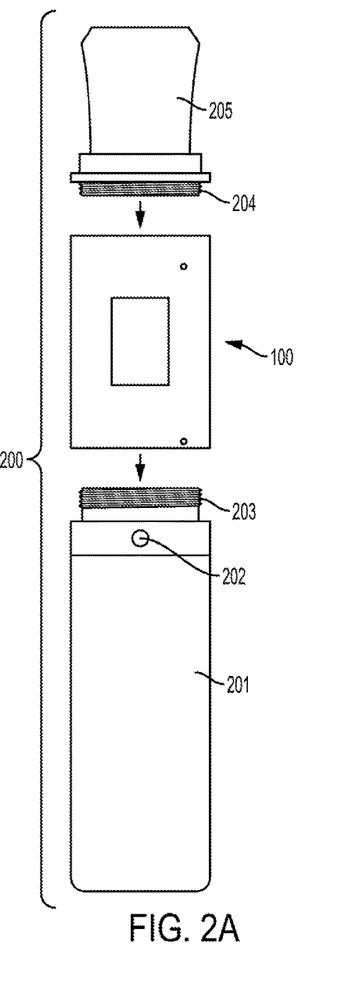
FIG. 2A is an exploded view showing the heating device shown in FIGS. 1A-1B in use with an electronic smoking device.
Figure 2B:
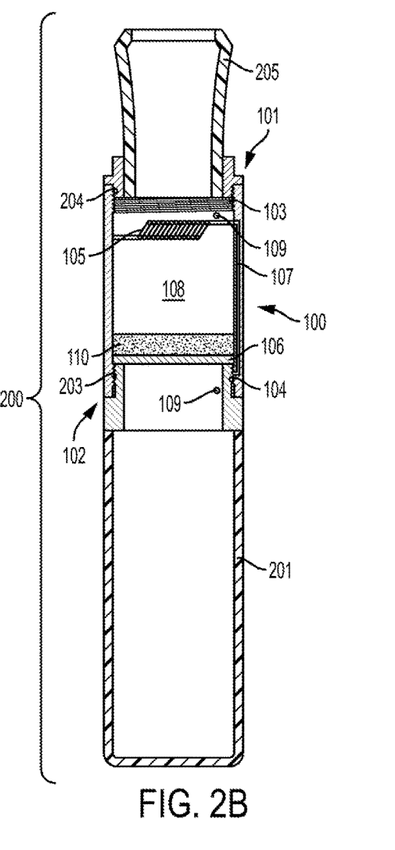
FIG. 2B is a cutaway assembled view showing the heating device shown in FIGS. 1A-1B in use with an electronic smoking device.

With reference to FIGS. 2A and 2B, shown is the heating device 100 in use with an exemplary electronic smoking device 200. The configuration smoking device 200 is for exemplary purposes only, but in this case comprises a modular type vaporizer that includes a control section 201, heating device 100, and a mouthpiece 205. The control section 201 comprises a battery or other power supply and chipset to control the device 200. In some embodiments, the heating device 100 is removably and threadingly engaged at the lower connector end 102, via lower connector 104, with the control section 201 to provide a physical and electrical connection between the heating device 100 and the battery or power supply of the control unit 201. In some embodiments, the control section 201 has a male threaded attachment point 203 that engages the internally or female threaded lower connector 104 of the heating device 100. The opposite end of the heating device 100, i.e. at the upper connector end 101, the upper connector 103 has an internally or female threads. In some embodiments, the mouthpiece 205, heating device 100 and/or the control section 201 include external apertures and air passages to allow for the passage of air through the system in order to draw vapor, smoke, or aerosol there-through. The inhalant material is to be inserted into the heating device 100 such that it can be heated by the heating element 105 disposed there-above.

The electronic smoking device 200 is assembled first by threading the heating device 100 onto the control unit 201. In some embodiments the control unit 201 includes a battery or other power supply such that when the control unit 201 is connected to the heating device 100, an electronical connection is established between the control until 201 and the heating element 105 of the heating device 105. The mouthpiece 205, which is shown as having male threads 204, is threaded into the exemplary female threads of the upper connector 103 of the heating device 100 to provide an inhalation point from the user to access.

In use, the user loads the heating device with inhalant material, either through the access door 111 or other means. Then the user activates the electronic smoking device 200, typically by a control button 202, which applies electrical current to the heating element 105 inside the heating device 100, which generates heat in a broiler-type fashion given it is disposed above the internal storage area 108 wherein the inhalant material 110 is to be placed. Heat generated by the heating element 105 heats from above the inhalant material held in the internal storage area 108. The inhalant material then turns into a vapor, smoke, or aerosol to be inhaled by the user through air passages within the device and out of the mouthpiece 205. In some embodiments, air passes through the electronic smoking device 200 components and through the one or more air passages 109 of the heating device 100 such that the vapor, smoke, or aerosol is released and pulled out of the container 10 and through and out of the mouthpiece 205.

Figure 3A:
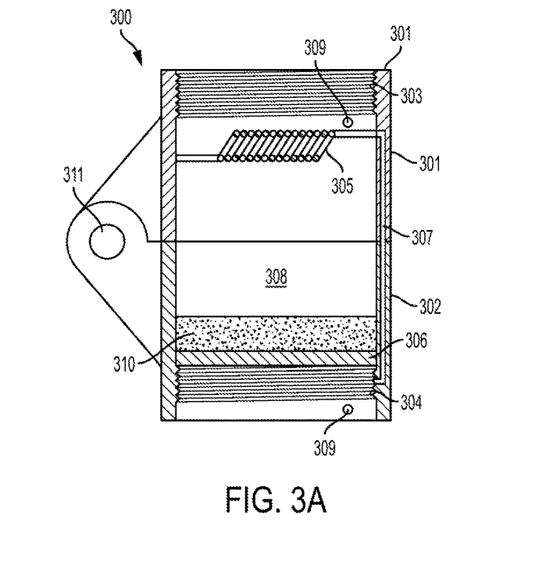
FIG. 3A is a cutaway view of another embodiment of the heating device.
Figure 3B:
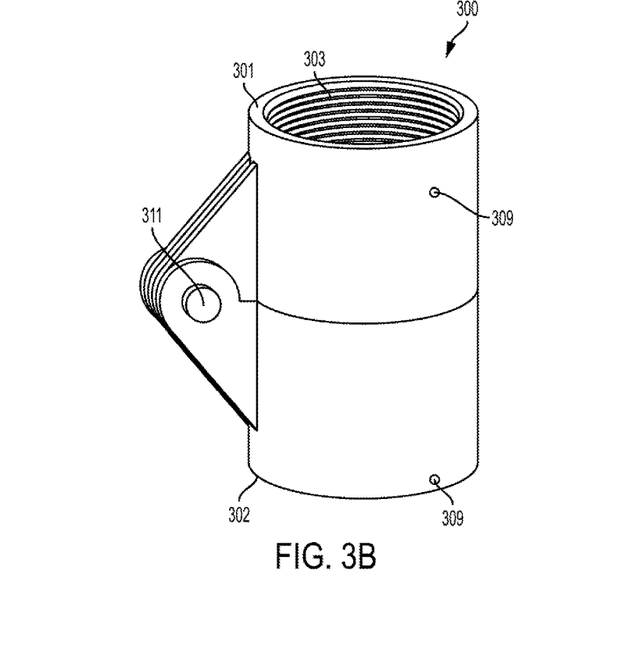
FIG. 3B is a perspective view of the heating device in FIG. 3A, in a closed position.
Figure 3C:
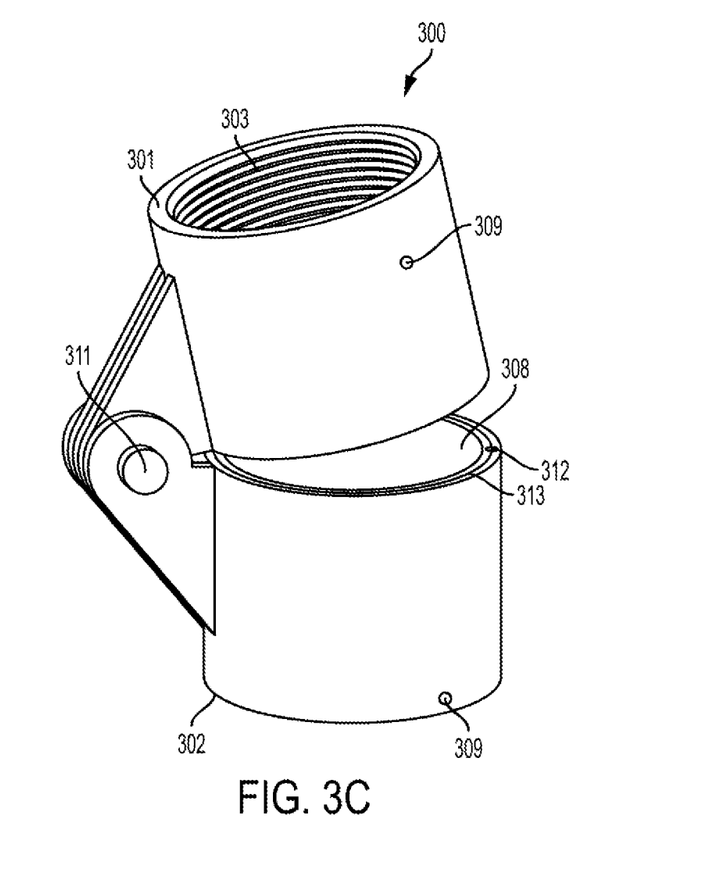
FIG. 3C is a perspective view of the heating device in FIG. 3A, in an open position.

With reference to FIGS. 3A-3C, shown is a two-piece heating device 300. The heating device 300 includes an upper heating chamber 301 and a lower storage cradle 302 that are removably connected such that chamber 301 and cradle 302 are at least partially separable from one another. In some embodiments the chamber 301 and cradle 302 are joined by a hinge 311; however, other connections are contemplated such threaded connections (see device 500 in FIGS. 5A-5B), magnetic connections, or a physical connection such as swivel mount rod so that the two pieces can swing across one another. In some embodiments, the chamber 301 and cradle 302 are generally cylindrical in shape and have matching dimensions. In some embodiments, either or both of the chamber 301 and cradle 302 include an air passage 309 to permit the passage of air therethrough.

In some embodiments, the upper portion of the chamber 301 has a connector 303, which may comprise internal or external threads, to accommodate a mouthpiece or other threaded component of an electronic smoking device. In other cases a mouthpiece may be attached to or inserted into the chamber 301 by other means such as a friction or interference fit. Disposed inside the chamber 301, which is located above the cradle 302, is a heating element 305. In some embodiments, the connector 303 is disposed above the heating element 305.

The cradle 302, disposed beneath the chamber 301, delimits an internal storage area 308 wherein inhalant material 310 (shown for exemplary purposes) may be placed. In some embodiments, the lower portion of the cradle 302 has a connector 304, which may comprise internal or external threads, to accommodate a battery or other power supply and/or a control unit. In some embodiments, the connector 304 is disposed below the internal storage area 308. In some embodiments, a partition 306 is disposed substantially toward the bottom of the internal storage area 308, which partition 306 functions as the floor, bottom, or shelf of the storage area 308 and separates same from the connector 304.

One or more air passages 309 are provided through the chamber 301 and/or cradle 302 which promote airflow through the heating device 300 while in use. The air passages 309 may be configured as apertures disposed through the components of the heating device 300 although other configurations are possible, such as a slots or bores located about the chamber 301 and/or cradle 302. Accordingly, in some embodiments the heating device 300 includes at least one air passage 309.

The heating element 305 in the chamber 301 is in electrical communication with the connector 304 of the cradle 302 such that the heating element 305 can be put into electrical communication with a battery or other power supply. In some embodiments, for example, an electrical connector 307 electrically couples the respective anode and cathode of the heating element to the connector 304, which connector 304 is configured as a respective anode and cathode connector to engage corresponding fittings on a battery or other power supply. As such, respective electrical connections may be deposed through both the chamber 301 and the cradle 302 to permit the transmission of current through such components. In some embodiments, corresponding releasable electrical contacts 312 are disposed on each of the chamber 301 and the cradle 302 at the junction thereof to complete the circuit when the two parts are attached. In some embodiments, a magnetic element 313 may disposed at or about each of the respective electrical contacts 312 to facilitate the physical and electrical connection between the chamber 301 and the cradle 302. The electrical connector 307 is not limited in configuration, however in some examples it may comprise wiring or a ribbon-type electrical conduit disposed in the sidewall (in the vicinity of where call out 307 points) of the components of the device 300.

Figure 4A:
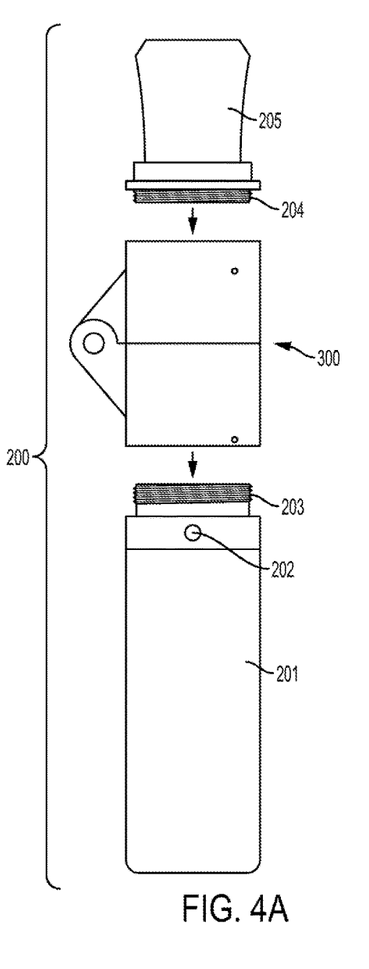
FIG. 4A is an exploded view showing the heating device shown in FIGS. 3A-3C in use with an electronic smoking device.
Figure 4B:
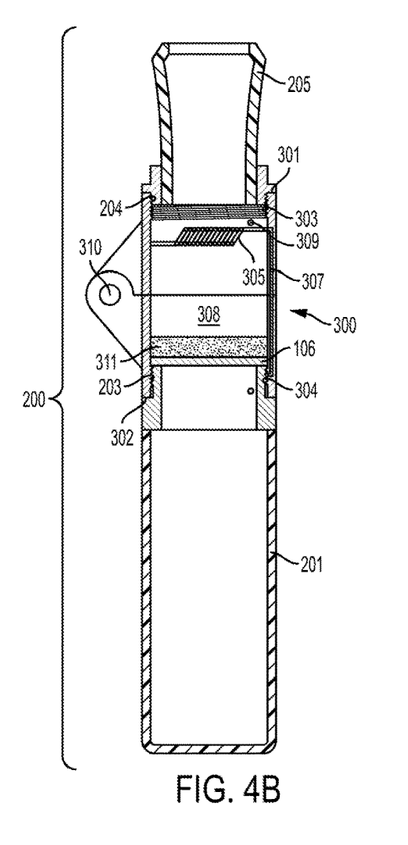
FIG. 4B is a cutaway assembled view showing the heating device shown in FIGS. 3A-3C in use with an electronic smoking device.

With reference to FIGS. 4A and 4B, shown is the heating device 300 in use with an exemplary electronic smoking device 200, similar to that shown in FIGS. 2A-2B. The heating device 300 functions with respect to the electronic smoking device 200 substantially as described here with respect to heating device 100, except that the inhalant material is loaded into the internal storage area 308 of the cradle 302 by temporarily separating the chamber 301 from the cradle 302 in order to gain access to the internal storage area 308.

Figure 5A:
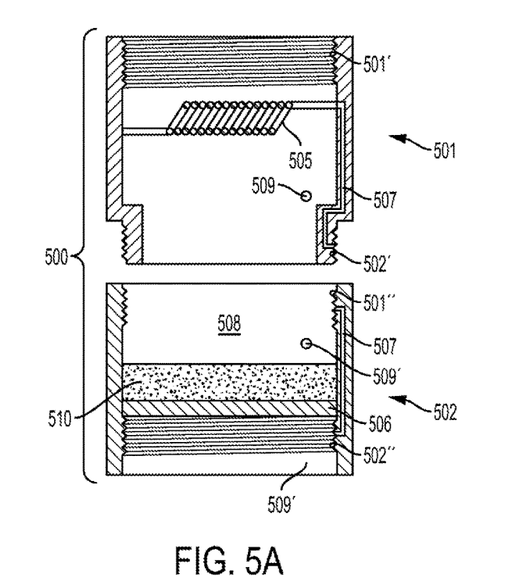
FIG. 5A is a cutaway view of yet another embodiment of the heating device.
Figure 5B:
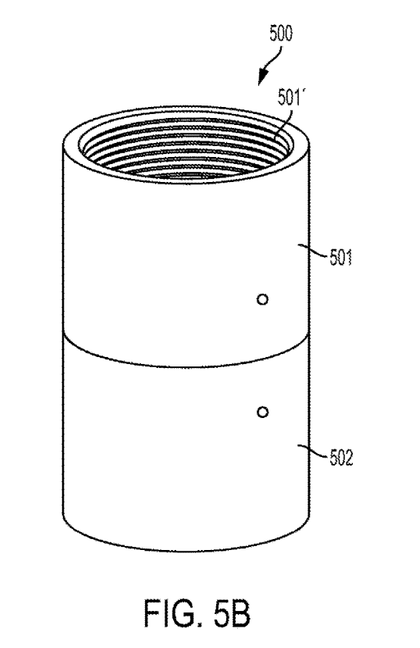
FIG. 5B is a perspective view of the assembled heating device shown in FIG. 5A.

With reference to FIGS. 5A-5B shown does yet another embodiment comprise a two-piece heating device 500. The heating device 500 includes an upper heating chamber 501 and a lower storage cradle 502 that are removably connected such that chamber 501 and cradle 502 are at least partially separable from one another. In some embodiments the chamber 501 and cradle 502 are joined by a corresponding threaded connectors 502' and 501", respectively; however, other connections such as snap-fit, interference fit, spring-biased engagement or the like are equally suitable. In some embodiments, the chamber 501 and cradle 502 are generally cylindrical in shape and have matching dimensions. In some embodiments, either or both of the chamber 501 and cradle 502 include an air passage 509 to permit the passage of air therethrough.

In some embodiments, chamber 501 includes an upper connector 501' and a lower connector 502', each of which may comprise internal or external threads. The upper connector 501' can be used to accommodate a mouthpiece or other threaded component of an electronic smoking device; In other cases a mouthpiece may be attached to or inserted into the chamber 301 by other means such as a friction or interference fit. The lower connector 502' is configured to engage the cradle 502, although it can also be used to engage other components of an electronic smoking device. Disposed inside the chamber 501, which is disposed above the cradle 502, is a heating element 505. In some embodiments, the upper connector 501' is disposed above the heating element 505 and the lower connector 502' is disposed below the heating element 505.

The cradle 502, configured to be disposed beneath and removably attached to the chamber 501, delimits an internal storage area 508 wherein inhalant material 510 (shown for exemplary purposes) may be placed. The cradle 502 includes an upper connector 501" and a lower connector 502", each of which may comprise internal or external threads. The upper connector 501" is configured to engage the lower connector 502' of the chamber 501, or another intermediate component. The lower connector 502" is configured to engage a battery or other power supply and/or a control unit. In some embodiments, the upper connector 501" is disposed above the internal storage area 508 and the lower connector 502" is disposed below the internal storage area 508. In some embodiments, a partition 506 is disposed substantially toward the bottom of the internal storage area 508, which partition 506 functions as the floor, bottom, or shelf of the storage area 508 and separates same from the lower connector 502".

One or more air passages 509 are provided through the chamber 501 and/or cradle 502 which promote airflow through the heating device 500 while in use. The air passages 509 may be configured as apertures disposed through the components of the heating device 500 although other configurations are possible, such as a slots or bores located about the chamber 501 and/or cradle 502. Accordingly, in some embodiments the heating device 500 includes at least one air passage 509.

The heating element 505 in the chamber 501 is in electrical communication with the upper connector 501' of the cradle 502 and, in turn, the lower connector 502" of the cradle 502 such that the heating element 505 can be put into electrical communication with a battery or other power supply. In some embodiments, for example, an electrical connector 507 electrically couples the respective anode and cathode of the heating element to the lower connector 502' of the chamber 501, which connector 502' is configured as a respective anode and cathode connector to engage corresponding fittings the upper connector 501" of the cradle 502. Another electrical connector 507 couples the upper connector 501" of the cradle 502 to the lower connector 502" of the cradle 502 such that the heating device 500 can receive power from a battery or other power supply. As such, respective electrical connections may be deposed through both the chamber 501 and the cradle 502 to permit the transmission of current through such components. The electrical connectors 507 are not limited in configuration, however in some examples it may comprise wiring or a ribbon-type electrical conduit or other electrically conductive material disposed in the sidewall (in the vicinity of where call out 507 points) of the components of the device 500.

Figure 6A:
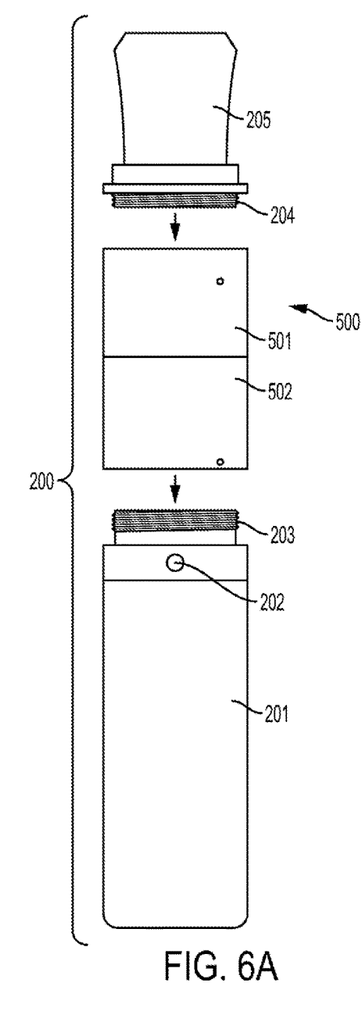
FIG. 6A is an exploded view showing the heating device shown in FIGS. 5A-5B in use with an electronic smoking device.
Figure 6B:
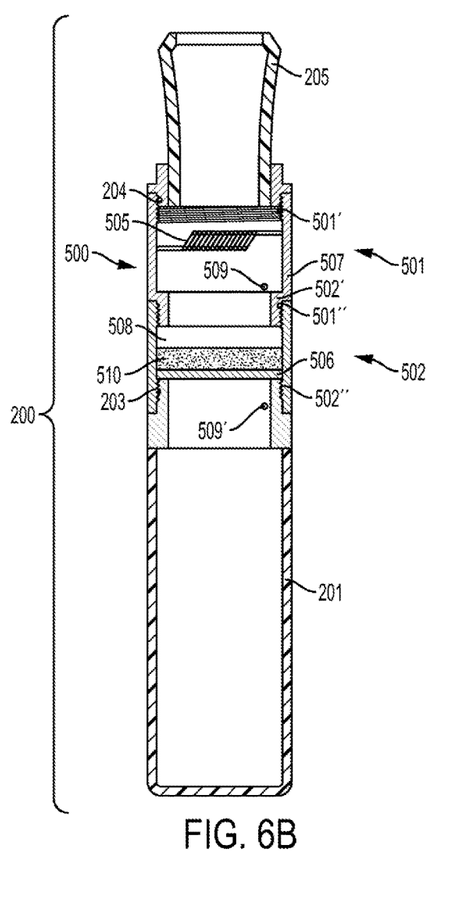
FIG. 6B is a cutaway assembled view showing the heating device shown in FIGS. 5A-5B in use with an electronic smoking device.

With reference to FIGS. 6A and 6B, shown is the heating device 500 in use with an exemplary electronic smoking device 200, similar to that shown in FIGS. 2A-2B. The heating device 500 functions with respect to the electronic smoking device 200 substantially as described here with respect to heating device 100 (and heating device 300), except that the inhalant material is loaded into the internal storage area 508 of the cradle 502 by temporarily decoupling the chamber 501 from the cradle 502 in order to gain access to the internal storage area 508.

It is appreciated that the present invention provides a top-down broiler-type heating device that is dissimilar from known heater or baking-type devices that locate the heating element below the inhalant material and rely either on conduction (i.e. direct contact) or convection from below. The broiler configuration disclosed herein is useful in limiting direct contact between the inhalant material and the heating element because the heating element is not in a position where the inhalant material can spill over or fall onto it. This limiting of direct contact provides safety and convenience benefits in that a toxic reaction is limited or avoided, and the heating element will tend to accumulate less residue than other systems. Additionally, the broiler configuration can improve heating consistency and speed and can more thoroughly and completely heat and exhaust a given portion of inhalant material. The broiler-type configuration also has the further advantage of improving flavor and vapor (or smoke or aerosol) concentration as it provides a cleaner heating process given the cumulative effects of these advantages.

As disclosed herein, the heating elements 105, 305, and 505 of the various embodiments may comprise known heat conductive wires, ribbons, traces, or other like electrically excitable heating implements. In some embodiments, the heating element comprises a encased heating element such as that described in Applicant's U.S. patent application Ser. Nos. 13/999,652, 15/298,147, 15/786,364, and 15/796,618, each of which are incorporated herein by reference. The selection of an encased heating element, such as a heating element comprising a wire encased in a quartz or other semi-precious gem material, further enhances the safety and usability of the heating device by preventing direct contact between the inhalant material and the heating wire of the heating element that can result in a toxic reaction and buildup of residue on the heating device components. The avoidance of direct contact between the inhalant material and the heating element also has the further advantage of improving flavor and vapor (or smoke or aerosol) concentration as it provides a cleaner reaction. Any of these heating elements, whether encased or not, can be implemented into the heating devices described herein to initiate a heating, vaporization (phase change), or combustion reaction inside the device.

In addition to accepting loose inhalant material, the heating device of the present invention, in its various embodiments, are configured to accept one or more inhalant material containers such as those described in Applicant's U.S. patent application Ser. Nos. 15/832,582 and 15/885,614, each of which are incorporated herein by reference. Such inhalant materials containers comprise cup-like and tube-like inhalant material containers which are useful from a health and convenience standpoint in that the containers can be inserted and removed on-demand, obviating the need to manually insert inhalant material into the internal storage area of the heating devices. In some cases, such inhalant material contains also provides a health benefit in that they can at least partially prevent direct contact between the inhalant material and the heating element of the heating device, thereby preventing a potentially toxic reaction between the inhalation material and the heating element. Limiting direct contact between the inhalant material and the heating element also has the further advantage of improving flavor and vapor (or smoke or aerosol) concentration as it provides a cleaner reaction.

As discussed herein, the various connector elements of the embodiments of the heating devices can, in some embodiments, function to provide both a physical connection between components and an electrical connection between components. In some embodiments, the connectors are configured with the aforementioned electrical contacts and/or anode/cathode configuration that interconnect and electrically couple the anode/cathode of the heating element to the anode/cathode of the battery or other power supply. In some embodiments, such as those shown herein, at least one or more of the connectors is threaded. However, the present invention is not limited to threaded connectors as other physical connections means are equally suitable such as interference fits, snap-fits, spring-biased fits, magnetic connections, and combinations thereof and the like.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise. Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means. The enumerated listing of items does not imply that any or all of the items are mutually exclusive, unless expressly specified otherwise. The terms "a", "an" and "the" mean "one or more", unless expressly specified otherwise. Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed, is:

1. A heating device for an electronic smoking device, comprising a heating element disposed above an internal storage area, the internal storage area configured to receive inhalant material to be at least partially heated by the heating element, and including an access door disposed about the internal storage area to facilitate access to the internal storage area.

2. A heating device for an electronic smoking device, comprising:
   a chamber removably connected to a cradle, wherein the chamber is disposed above the cradle;
   a heating element disposed in the chamber;
   an internal storage area disposed in the cradle, the internal storage area configured to receive inhalant material to be at least partially heated by the heating element; and
   including an access door disposed about the internal storage area.

3. A heating device for an electronic smoking device, comprising:
   a chamber removably connected to a cradle, wherein the chamber is disposed above the cradle;
   a heating element disposed in the chamber;
   an internal storage area disposed in the cradle, the internal storage area configured to receive inhalant material to be at least partially heated by the heating element; and
   wherein the chamber and the cradle are removably connected by a hinge.

4. A heating device for an electronic smoking device, comprising:
   a chamber removably connected to a cradle, wherein the chamber is disposed above the cradle;
   a heating element disposed in the chamber;
   an internal storage area disposed in the cradle, the internal storage area configured to receive inhalant material to be at least partially heated by the heating element; and
   wherein the chamber and cradle are removably connected by a threaded connection.

5. A heating device for an electronic smoking device, comprising:
   a chamber removably connected to a cradle, wherein the chamber is disposed above the cradle;
   a heating element disposed in the chamber;
   an internal storage area disposed in the cradle, the internal storage area configured to receive inhalant material to be at least partially heated by the heating element; and
   wherein the chamber and the cradle are removably connected by a magnetic connection.

* * * * *